US007763208B2

(12) United States Patent  (10) Patent No.: US 7,763,208 B2
Steichen et al.  (45) Date of Patent: Jul. 27, 2010

(54) SYSTEM AND METHOD FOR SENSING AND ANALYZING GASES

(75) Inventors: John Carl Steichen, Landenberg, PA (US); Harry Edwards Betsill, Parkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 1048 days.

(21) Appl. No.: 10/978,773

(22) Filed: Nov. 1, 2004

(65) Prior Publication Data

US 2007/0202012 A1    Aug. 30, 2007

Related U.S. Application Data

(60) Provisional application No. 60/519,433, filed on Nov. 12, 2003.

(51) Int. Cl.
*G01N 30/96* (2006.01)
(52) U.S. Cl. ...................................................... 422/88
(58) Field of Classification Search .................... 422/88
See application file for complete search history.

(56) References Cited

U.S. PATENT DOCUMENTS

| | | | |
|---|---|---|---|
| 4,457,161 A | | 7/1984 | Iwanaga |
| 4,542,640 A | * | 9/1985 | Clifford ..................... 73/31.06 |
| 4,554,639 A | | 11/1985 | Baker |
| 4,847,783 A | | 7/1989 | Grace |
| 5,132,541 A | | 7/1992 | Conrads |
| 5,426,934 A | | 6/1995 | Hunt |
| 5,681,997 A | * | 10/1997 | McHale et al. ................. 73/727 |
| 5,832,411 A | | 11/1998 | Schatzmann |
| 6,085,576 A | | 7/2000 | Sunshine |
| 6,170,318 B1 | | 1/2001 | Lewis |
| 6,849,239 B2 | | 2/2005 | Morris |
| 6,890,715 B1 | | 5/2005 | Lewis |
| 7,231,290 B2 | | 6/2007 | Steichen |
| 2002/0017467 A1 | | 2/2002 | Ando |
| 2002/0121440 A1 | | 9/2002 | Morris |
| 2005/0063873 A1 | | 3/2005 | Morris |
| 2006/0108220 A1 | | 5/2006 | Betsill |
| 2007/0202012 A1 | | 8/2007 | Steichen |

FOREIGN PATENT DOCUMENTS

WO    WO 01/61298 A1 *   8/2001

OTHER PUBLICATIONS

International Search Report and Written Opinion in PCT/US2004/037594, Jun. 14, 2005 (for application published as WO 2005/047876).
Byung-Su Joo et al, Pattern Recognition of Gas Sensor Array Using Characteristics of Impedence, *Sensors and Actuators*, B 77 (2001) 209~214, Elsevier, New York.

(Continued)

*Primary Examiner*—Walter D Griffin
*Assistant Examiner*—Bobby Ramdhanie

(57) ABSTRACT

Disclosed herein is a device and method for converting the resistances of an array of metal oxide sensors into digital signals, wherein the sensors respond to the concentration of gases surrounding the sensor array. The device includes an electronic excitation device that provides an excitation voltage to the sensors; analog-to-digital signal conversion devices that convert the resistances of the sensors to digital signals; and means for calculating gas concentrations from the digital signals.

30 Claims, 11 Drawing Sheets

OTHER PUBLICATIONS

Albert, et al., "Cross-Reactive Chemical Sensor Arrays", Chem. Rev. 2000, (2000), pp. 2595-2626, vol. 100, California.

Getino, et al., "Integrated sensor array for gas analysis in combustion atmospheres", Sensors and Actuators (1996), pp. 128-133, vol. B 33, Spain.

Di Natale, et al., "Study of the effect of the sensor operating temperature on SnO2-based sensor-array performance", Sensors and Actuators (1995), pp. 187-191, vol. B 23, Italy.

Di Natale, et al., "Performance evaluation of an SnO2-based sensor array for the quantitative measurement of mixtures H2S and NO2", Sensors and Actuators (1994), pp. 217-224, vol. B 20, Italy.

H. Meixner, et al., "Metal oxide sensors", Sensors and Actuators (1996), pp. 198-202, vol. B 33, Germany.

H. Meixner, et al., "Chemosensors for motor management systems of the future", Fresenius J Anal Chem. (1994), pp. 536-541, vol. 348, Germany.

* cited by examiner

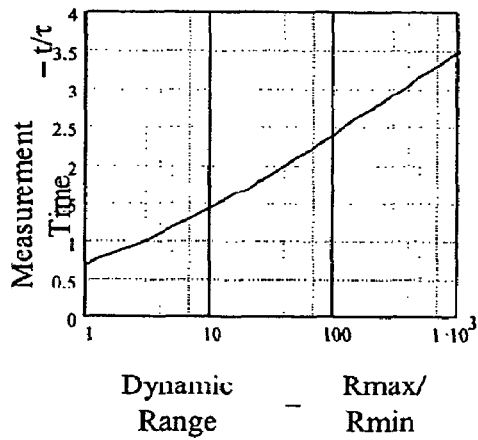
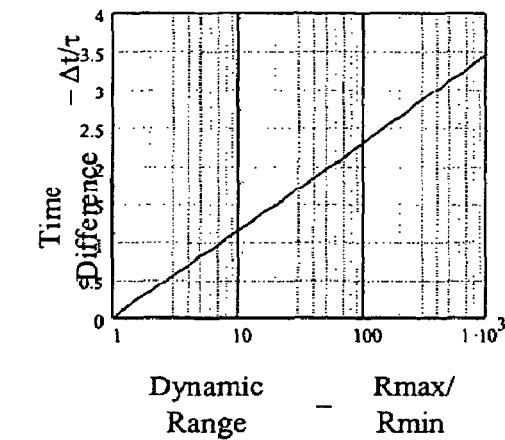
Fig. 7
Fig. 8
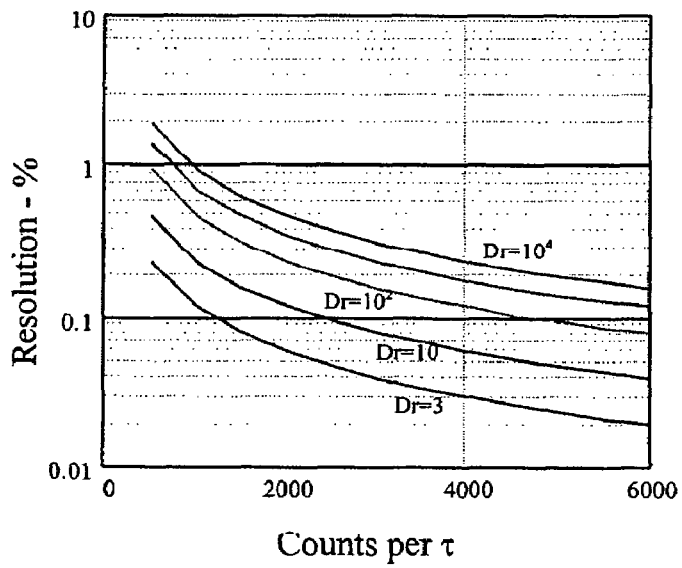
Fig. 9

SYSTEM AND METHOD FOR SENSING AND ANALYZING GASES

CROSS REFERENCE TO RELATED APPLICATIONS

The present application relates to U.S. patent application Ser. No. 10/117,472, filed Apr. 5, 2002, which is a continuation-in-part of U.S. patent application Ser. No. 09/977,791, filed Oct. 15, 2001, which claimed the benefit of U.S. Provisional Application Ser. No. 60/240,619, filed Oct. 16, 2000, and U.S. Provisional Application Ser. No. 60/246,946, filed Nov. 9, 2000, the disclosures of the above-referenced applications being incorporated by reference herein in their entireties.

BACKGROUND OF THE INVENTION

A. Field of the Invention

The present invention relates generally to a system and method for sensing and analyzing certain gases, including $NO_x$, hydrocarbons, carbon monoxide and oxygen in a multi-component gas system using chemical sensors and chemical sensor arrays.

B. Description of the Related Art

The use of chemical sensing devices to detect certain gases is known. Many attempts have been made to find a material with selectivity and sensitivity for a specific gas. For example, U.S. Pat. No. 4,535,316 discloses a resistive sensor for measuring oxygen. See also H. Meixner et al., *Sensors and Actuators B: Chem.*, vol. 33, pp. 198-202 (1996). It is apparent that different materials must be used for each gas to be detected. However, when a gas is part of a multi-component system, using one material to detect a specific gas is difficult because of the cross-sensitivities of the material to the various component gases of the mixture.

One example of a multi-component gaseous system is a combustion gas emission, which can include oxygen, carbon monoxide, nitrogen oxides, hydrocarbons, $CO_2$, $H_2S$, sulfur dioxide, hydrogen, water vapor, halogens and ammonia. See H. Meixner et al., *Fresenius' J. Anal. Chem.*, vol. 348, pp. 536-541 (1994). In many combustion processes, there is a need to determine whether the gas emissions meet requirements established by federal and state air quality regulations in various jurisdictions. Several types of gas sensors have been developed to address this need. See U.S. Pat. No. 5,630,920, which discloses an electrochemical oxygen sensor; U.S. Pat. No. 4,770,760, which discloses a sensor for detecting oxygen and oxides of nitrogen; and U.S. Pat. No. 4,535,316, which discloses a resistive sensor for measuring oxygen. It would be advantageous to be able to simultaneously analyze two or more components of a mixture such as a combustion gas emission, to calculate concentration for example, in terms only of data generated by direct contact of the gases with a sensor and without having to separate any of the gases in the mixture. Prior art methods do not currently meet this need.

Numerous sensors have been disclosed to detect gases evolving from foods and from other relatively low temperature applications. See K. Albert et al., *Chem. Rev.*, vol. 200, pp. 2595-2626 (2000). Arrays of several undoped and doped tin oxide sensors have also been disclosed for use in detecting various combustion gases up to 450° C. See C. DiNatale et al., *Sensors and Actuators B: Chem.*, vol. 20, pp. 217-224 (1994); J. Getino et al., *Sensors and Actuators B: Chem.*, vol. 33, pp. 128-133 (1996); and C. DiNatale et al., *Sensors and Actuators B: Chem.*, vol. 23, pp. 187-191 (1995). However, at higher temperatures and in the highly corrosive environment in which one would use chemical sensors to monitor combustion gases, operating temperature can alter or impair the performance of the sensor array. That being the case, high temperature environments require the use of materials that are both chemically and thermally stable and that maintain measurable responses to the gases of interest. The effect of the operating temperature on the response of tin oxide-based sensor arrays was studied up to 450° C. See C. DiNatale et al., *Sensors and Actuators B: Chem.*, vol. 23, pp. 187-191 (1995). However, materials in addition to those previously known in the art are still needed to be able to provide a system and method capable of directly monitoring the gas emissions of multi-component gas systems at higher temperatures, such as would be encountered in the operation of combustion gas systems. Detecting circuits and analytical devices are also needed for such chemical sensors to provide a system and method capable of processing the chemical sensor outputs and providing useful information in determining the components and constituents of the monitored multi-component gas system.

Addressing this need would permit the use of a chemical sensor to measure combustion emissions, such as automobile exhausts, and determine whether those emissions meet functional and mandated requirements. In addition, it has surprisingly been found that the system and method of this invention that are useful for analyzing high temperature gases, such as automotive emissions, may be employed with equal effect in analyzing low temperature gases.

SUMMARY OF THE INVENTION

The present invention satisfies these needs by providing a computer-implemented system and method for sensing and analyzing certain gases, including $NO_x$, hydrocarbons, carbon monoxide and oxygen in a multi-component gas system using novel chemical sensors and chemical sensor arrays, detecting circuits, and analytical devices.

Additional advantages of the invention will be set forth in part in the description which follows, and in part will be learned from the description, or may be learned by practice of the invention. The advantages of the invention will be realized and attained by means of the elements and combinations particularly pointed out in the appended claims, and equivalents thereof. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings:

FIGS. 7 and 8 are graphs showing the timing characteristics of the electrical circuit shown in FIG. 6 normalized to τ as a function of the dynamic range of Rm and Dr, where FIG. 7 provides the total time (t) for the measurement and FIG. 8 provides the time difference (Δt) for the measurement;

FIG. 9 is a graph showing the resolutions, in percents, as a function of the precision of the τ measurement, in counts, for the electrical circuit shown in FIG. 6;

DESCRIPTION OF EMBODIMENTS OF THE INVENTION

Reference will now be made in detail to the present embodiments of the invention, examples of which are illustrated in the accompanying drawings. Wherever possible, the same reference numbers will be used throughout the drawings to refer to the same or like parts.

Figure 1:
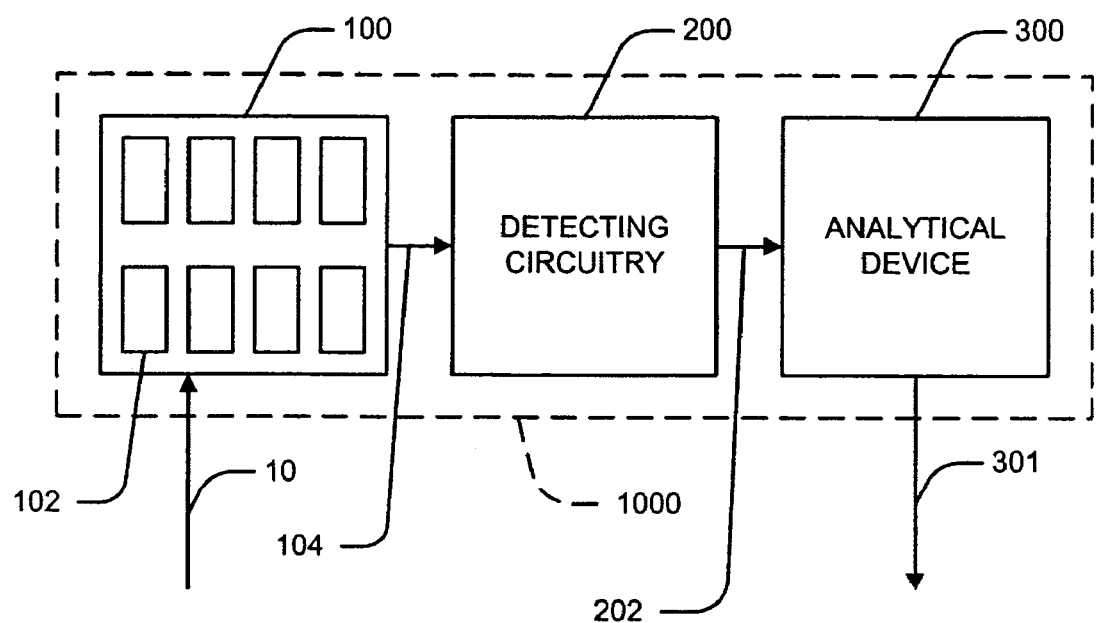
FIG. 1 is a schematic diagram showing a system of the present invention, the system including a chemical sensor array, detecting circuitry, and an analytical device.

The present invention is broadly drawn to a system and method for directly sensing gases in multi-component gas systems under ambient to high temperature conditions, as generally shown by reference numeral 1000 in FIG. 1. The system is also useful for simultaneously and directly measuring the concentration of at least one gas in a multi-component gas system at temperature ranges from about ambient to about 1000° C. By "directly sensing" is meant that the array will be present in the gas stream and the response will be a function of the concentrations of the gases themselves, and that the gases do not have to be physically separated in the gas stream in order to be detected. The system and method can be used to detect and measure the concentrations of combustion gases, such as oxygen, carbon monoxide, nitrogen oxides, hydrocarbons, such as butane, $CO_2$, $H_2S$, sulfur dioxide, halogens, and ammonia at lower and higher temperatures in automobile emissions. In this application, the system can be used at the high temperatures found in automotive emission systems, typically in the range of from about 450° C. to about 1000° C. In addition there are a variety of other combustion processes for which this system could be applied, including diesel engines and home heating. These applications make use of the detection of gases such as nitrogen oxides, carbon monoxide, hydrocarbons and oxygen at the ppm to percent levels, typically in a highly corrosive environment. This system and method is also useful for detecting gases in other gas systems such as those found in manufacturing processes, waste streams, and environmental monitoring.

The system described herein utilizes an array of sensing materials to detect the components of the gas system. By "array" is meant at least two different materials that are spatially separated. The materials used are chemo-electro-active materials. As used herein, "chemo-electro-active materials" are materials that have an electrical response to certain gases. Some metal oxide semiconducting materials, mixtures thereof, or mixtures of metal oxide semiconductors with other inorganic compounds are chemo-electro-active and are particularly useful in the system and method of the present invention. The various chemo-electro-active materials used herein exhibit changes to different degrees in the presence of different gases. As a result, an array of appropriately chosen chemo-electro-active materials can be used to determine the presence of certain gases in a gas stream. These chemo-electro-active materials can be used at temperatures from ambient to about 1000° C. Preferably, the mole percentages of the major components of these materials differ.

The measurement of the gas concentrations using chemo-electro-active materials can be based on the change in AC impedances of the materials in response to the concentration of adsorbed gas molecules at their surfaces, or can be based on, for example, capacitance, voltage, current, DC resistance or temperature differential. By using an array of these materials, a pattern of the respective responses can be used to simultaneously and directly measure the concentration of at least one gas in a multi-component gas system at temperature ranges from about ambient to about 1000° C.

As seen in FIG. 1, the system 1000 provides a chemical sensor or chemical sensor array comprising a substrate 100 and one or more chemo-electro-active materials 102 chosen to detect the presence and/or concentration of one or more gases in a multi-component gas stream 10. The system 1000 further comprises detecting circuitry 200 to detect changes in the AC impedances of the materials 104 in response to the concentration of adsorbed gas molecules at their surfaces. The system 1000 further comprises an analytical device 300 to measure or analyze the detected gases 202 such that the presence of the gases are identified and their concentrations are measured and outputted 301. Analytical device 300 may include instrumentation or equipment that is capable of performing chemometrics, neural networks or other pattern recognition techniques. In some embodiments, the analytical device 300 may be incorporated into the AC impedance determining circuitry 200. The system 1000 may further comprise a housing for substrate 100 and array of chemo-electro-active materials 102, the detecting circuitry 200, and analytical device 300, although analytical device 300 may be separate from the housing. The chemical sensors 100, detecting circuitry 200, and analytical device 300 will each be described in detail below.

A. The Chemical Sensors

The chemical sensor array 100 of the present invention is disclosed in U.S. patent application Ser. Nos. 10/117,472 and 09/977,791, referenced above and incorporated herein by reference. The array 100 may be situated within the gas mixture 10, and more particularly within the source of the gas mixture 10, if desired. Alternatively, the array 100 may reside in a chamber to which the gas mixture 10 is directed from its source at another location. When gas is directed to a chamber in which an array is located, the gas mixture may be inserted in and removed from the chamber by piping, conduits, or any other suitable gas transmission equipment.

A response may be obtained upon exposure of the gas-sensing materials to the multi-component gas mixture, and the response will be a function of the concentrations of one or more of the analyte gases themselves in the gas mixture. The sensor materials will be exposed substantially simultaneously to each of the analyte gases, and an analyte gas does not have to be physically separated from the multi-component gas mixture for an analysis of the mixture and/or one or more components thereof to be conducted. This invention can be used, for example, to detect and/or measure the concentrations of combustion gases, such as oxygen, carbon monoxide, nitrogen oxides, hydrocarbons such as butane, $CO_2$, $H_2S$, sulfur dioxide, halogens, hydrogen, water vapor and ammonia, at variable temperatures in automobile emissions.

The system and method are therefore useful at the higher temperatures found in automotive emission systems, typically in the range of from about 400° C. to about 1000° C. In addition there are a variety of other combustion processes for which this invention could be applied, including diesel engines and home heating. These applications require the detection of gases such as nitrogen oxides, ammonia, carbon monoxide, hydrocarbons and oxygen at the ppm to percent levels, typically in a highly corrosive environment. The apparatus and method are also useful for detecting gases in other gas systems such as those found in manufacturing processes, waste streams, and environmental monitoring; or in systems in which odor detection is important and/or that are at lower temperature, such as in the medical, agricultural or food and beverage industries.

Figure 2:
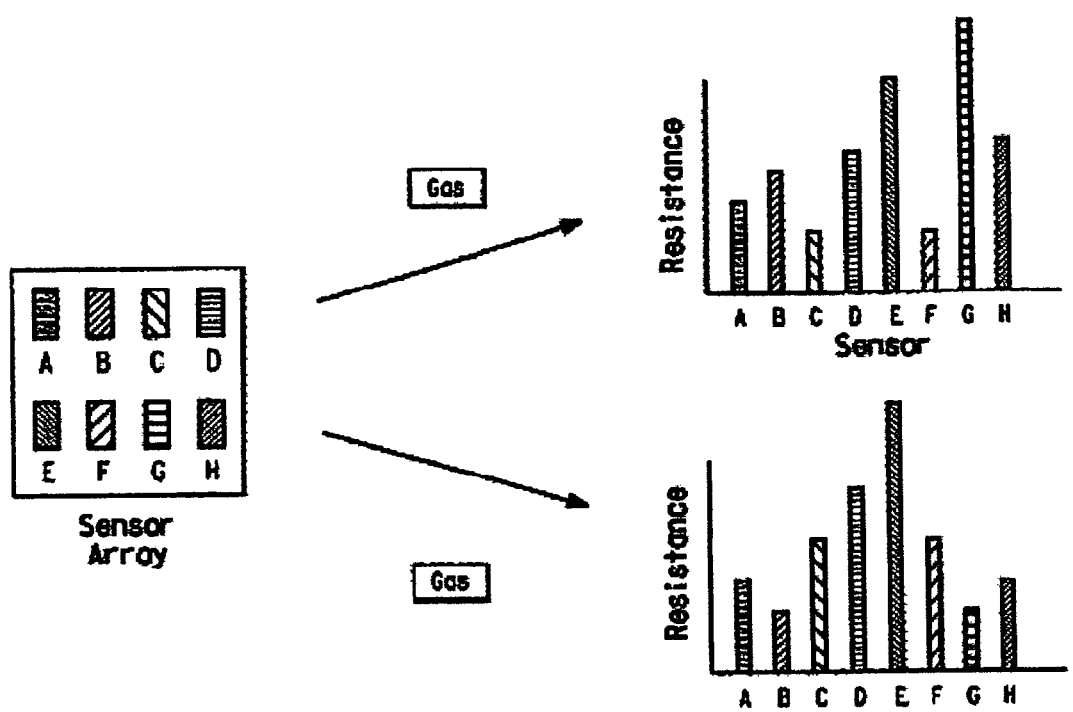
FIG. 2 depicts the sensor array concept of the system shown in FIG. 1.

The system and method utilize an array of sensing materials to analyze a gas mixture and/or the components thereof to, for example, detect the presence of and/or calculate the concentration of one or more individual analyte gas components in the system. By "array" is meant at least two different materials that are spatially separated, as shown for example in FIGS. 1 and 2. The array may contain, for example, 3, 4, 5, 6, 8, 10 or 12 gas-sensing materials, or other greater or lesser numbers as desired. It is preferred that there be provided at least one sensor material for each of the individual gases or subgroups in the mixture to be analyzed. It may be desirable, however, to provide more than one sensor material that is responsive to an individual gas component and/or a particular subgroup in the mixture. For example, a group of at least 2, 3, 4, 5, 6, 7, 8, 9, 10, 11 or 12 sensors could be used to detect the presence of, and/or calculate the concentration of, one or more individual component gases and/or one or more subgroups of gases in the mixture. Different groups of sensors could be used for this purpose, which may or may not have members in common. A subgroup of gases that is an analyte as the subgroup may or may not contain as a member an individual gas that is itself an analyte. Preferably, the mole percentages of the major components of each gas-sensing material differs from that of each of the others.

The sensing materials used are chemo-electro-active materials. A "chemo-electro-active material" is a material that has an electrical response to at least one individual gas in a mixture. Some metal oxide semiconducting materials, mixtures thereof, or mixtures of metal oxide semiconductors with other inorganic compounds are chemo-electro-active, and are particularly useful in this invention. Each of the various chemo-electro-active materials used herein preferably exhibits an electrically-detectable response of a different kind and/or extent, upon exposure to the mixture and/or an analyte gas, than each of the other chemo-electro-active materials. As a result, an array of appropriately chosen chemo-electro-active materials can be used to analyze a multi-component gas mixture, such as by interacting with an analyte gas, sensing an analyte gas, or determining the presence and/or concentration of one or more analyte gases in a mixture, despite the presence therein of interfering gases that are not of interest.

The system and method are useful for detecting those gases that are expected to be present in a gas stream. For example, in a combustion process, gases that are expected to be present include oxygen, nitrogen oxides (such as NO, $NO_2$, $N_2O$ or $N_2O_4$), carbon monoxide, hydrocarbons (such as $C_nH_{2n+2}$, and the same may be saturated or unsaturated, or be optionally substituted with hetero atoms; and cyclic and aromatic analogs thereof), ammonia or hydrogen sulfide, sulfur dioxide, $CO_2$, or methanol. Other gases of interest may include alcohol vapors, solvent vapors, hydrogen, water vapor, and those deriving from saturated and unsaturated hydrocarbons, ethers, ketones, aldehydes, carbonyls, biomolecules and microorganisms. The component of a multi-component gas mixture that is an analyte of interest may be an individual gas such as carbon monoxide; may be a subgroup of some but not all of the gases contained in the mixture, such as the nitrogen oxides ($NO_x$); or may be a combination of one or more individual gases and one or more subgroups. When a subgroup of gases is an analyte, a chemo-electro-active material will respond to the collective concentration within a multi-component gas mixture of the members of the subgroup together.

Obtaining information related to the compositional content of a gas mixture using these sensor materials, such as measurement of gas concentrations, can be based on a change in an electrical property, such as AC impedance, of at least one, but preferably each and all, of the materials upon exposure of the materials to a mixture containing one or more analyte gases. Analysis of a gas mixture can also be performed in terms of extent of change in other electrical properties of the sensor materials, such as capacitance, voltage, current or AC or DC resistance. Change in DC resistance may be determined, for example, by measuring change in temperature at constant voltage. The change in one of these illustrative properties of a sensor material is a function of the partial pressure of an analyte gas within the gas mixture, which in turn determines the concentration at which the molecules of the analyte gases become adsorbed on the surface of a sensor material, thus affecting the electrical response characteristics of that material. By using an array of chemo-electro-active materials, a pattern of the respective responses exhibited by the materials upon exposure to a mixture containing one or more analyte gases can be used to simultaneously and directly detect the presence of, and/or measure the concentration of, at least one gas in a multi-component gas system. The invention, in turn, can be used to determine the composition of the gas system. The concept is illustrated schematically in FIGS. 1 and 2, and is exemplified below.

To illustrate, consider the theoretical example below of the exposure of a sensor material to a mixture containing an analyte gas. Where a response is obtained, the event is depicted as positive (+), and where no response is obtained, the event is depicted as negative (−). Material 1 responds to Gas 1 and Gas 2, but shows no response to Gas 3. Material 2 responds to Gas 1 and Gas 3, but shows no response to Gas 2, and Material 3 responds to Gas 2 and Gas 3, but shows no response to Gas 1.

|  | Material 1 | Material 2 | Material 3 |
| --- | --- | --- | --- |
| Gas 1 | + | + | − |
| Gas 2 | + | − | + |
| Gas 3 | − | + | + |

Therefore, if an array consisting of Materials 1, 2, and 3 gives the following response to an unknown gas,

|  | Material 1 | Material 2 | Material 3 |
| --- | --- | --- | --- |
| Unknown Gas | + | − | + | then the unknown gas would be identified as Gas 2. The response of each sensor material would be a function of the partial pressure within the mixture of, and thus the concentration of, an analyte gas or the collective concentration of a subgroup of analyte gases; and the response could be quantified or recorded as a processible value, such as a numerical value. In such case, the values of one or more responses can be used to generate quantitative information about the concentration within the mixture of one or more analyte gases.

The chemo-electro-active material can be of any type, but especially useful are semiconducting metal oxides such as $ZnO$, $TiO_2$, $WO_3$, and $SnO_2$. These particular materials are advantageous due to their chemical and thermal stability. The chemo-electro-active material can be a mixture of two or more semiconducting materials, or a mixture of a semiconducting material with an inorganic material, or combinations thereof. The semiconducting materials of interest can be deposited on a suitable solid substrate that is an insulator such as, but not limited to, alumina or silica and is stable under the conditions of the multi-component gas mixture. The array then takes the form of the sensor materials as deposited on the substrate. Other suitable sensor materials include single crystal or polycrystalline semiconductors of the bulk or thin film type, amorphous semiconducting materials, and semiconductor materials that are not composed of metal oxides.

The chemo-electro-active materials used as sensor materials in this invention may, for example, be metal oxides of the formula $M^1O_x$, $M^1_aM^2_bO_x$, or $M^1_aM^2_bM^3_cO_x$; or mixtures thereof, wherein $M^1$, $M^2$ and $M^3$ are metals that form stable oxides when fired in the presence of oxygen above 500° C.; $M^1$ is selected from Periodic Groups 2-15 and the lanthanide group; $M^2$ and $M^3$ are independently selected from Periodic Groups 1-15 and the lanthanide group, but $M^2$ and $M^3$ are not the same in $M^1_aM^2_bM^3_cO_x$; a, b, and c are each independently in the range of about 0.0005 to about 1; and x is a number sufficient so that the oxygen present balances the charges of the other elements in the compound.

The metal oxides that contain more than one metal do not have to be a compound or solid solution, but can be a mixture of discrete metal oxides. They may exhibit composition gradients, and can be crystalline or amorphous. Suitable metal oxides are those that: (1) when at a temperature of about 400° C. or above, have a resistivity of about 1 to about $10^6$ ohm-cm, preferably about 1 to about $10^5$ ohm-cm, and more preferably about 10 to about $10^4$ ohm-cm; (2) show a chemo/electro response to at least one gas of interest; and (3) are stable and have mechanical integrity, that is are able to adhere to the substrate and not degrade at the operating temperature. The metal oxides may also contain minor or trace amounts of hydration and elements present in the precursor materials.

In certain preferred embodiments, the metal oxide materials may include those in which: $M^1$ is selected from the group consisting of Ce, Co, Cu, Fe, Ga, Nb, Ni, Pr, Ru, Sn, Ti, Tm, W, Yb, Zn, and Zr; and/or $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$.

In certain other preferred embodiments, the metal oxide materials may include those in which:

$M^1O_x$ is $Ce_aO_x$, $CoO_x$, $CuO_x$, $FeO_x$, $GaO_x$, $NbO_x$, $NiO_x$, $PrO_x$, $RuO_x$, $SnO_x$, $Ta_aO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive; and/or $M^1_aM^2_bO_x$ is $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Ci_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aLa_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, $Sb_aSn_bO_x$ with frit additive, $Ta_aTi_bO_x$ with frit additive, or $Ti_aZn_bO_x$ with frit additive; and/or $M^1_aM^2_bM^3_cO_x$ is $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$.

In certain other preferred embodiments, the metal oxide materials may include those that are in an array of first and second chemo-electro-active materials, wherein the chemo-electro-active materials are selected from the pairings in the group consisting of (i) the first material is $M^1O_x$, and the second material is $M^1_aM^2_bO_x$;

(ii) the first material is $M^1O_x$, and the second material is $M^1_aM^2_bM^3_cO_x$;

(iii) the first material is $M^1_aM^2_bO_x$, and the second material is $M^1_aM^2_bM^3_cO_x$;

(iv) the first material is a first $M^1O_x$, and the second material is a second $M^1O_x$;

(v) the first material is a first $M^1_aM^2_bO_x$, and the second material is a second $M^1_aM^2_bO_x$; and (vi) the first material is a first $M^1_aM^2_bM^3_cO_x$, and the second material is a second $M^1_aM^2_bM^3_cO_x$;

wherein $M^1$ is selected from the group consisting of Ce, Co, Cu, Fe, Ga, Nb, Ni, Pr, Ru, Sn, Ti, Tm, W, Yb, Zn, and Zr; $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr, but $M^2$ and $M^3$ are not the same in $M^1_aM^2_bM^3_cO_x$; a, b and c are each independently about 0.0005 to about 1; and x is a number sufficient so that the oxygen present balances the charges of the other elements in the compound.

The sensor materials may optionally contain one or more additives to promote adhesion to a substrate, or that alter the conductance, resistance or selectivity of the sensor material. Examples of additives to promote adhesion are frits, which are finely ground glass, or finely ground inorganic minerals that are transformed into glass or enamel on heating. Illustrative frits include those designated as F2834, F3876, F2967, KH770, KH710 and KH375, available from DuPont iTechnologies. These may be used in amounts of up to 30 volume percent of the composition from which the sensor material is made. Examples of additives to alter the conductance, resistance, or selectivity include Ag, Au, or Pt, as well as frits.

If desired, the sensor materials may also contain additives that, for example, catalyze the oxidation of a gas of interest or promote the selectivity for a particular analyte gas; or contain one or more dopants that convert an n semiconductor to a p semiconductor, or vice versa. These additives may be used in amounts of up to 30 weight percent of the composition from which the sensor material is made. Any frits or other additives used need not be uniformly or homogeneously distributed throughout the sensor material as fabricated, but may be localized on or near a particular surface thereof as desired. Each chemo-electro-active material may, if desired, be covered with a porous dielectric overlayer. A suitable overlayer is QM44 from DuPont iTechologies.

Any method of depositing the chemo-electro-active material to a substrate is suitable. One technique used for deposition is applying a semiconducting material on an alumina substrate on which electrodes are screen printed. The semiconducting material can be deposited on top of electrodes by hand painting semiconducting materials onto the substrate, nanopipetting materials into wells, thin film deposition, or thick film printing techniques. Most techniques are followed by a final firing to sinter the semiconducting materials.

Figure 3:
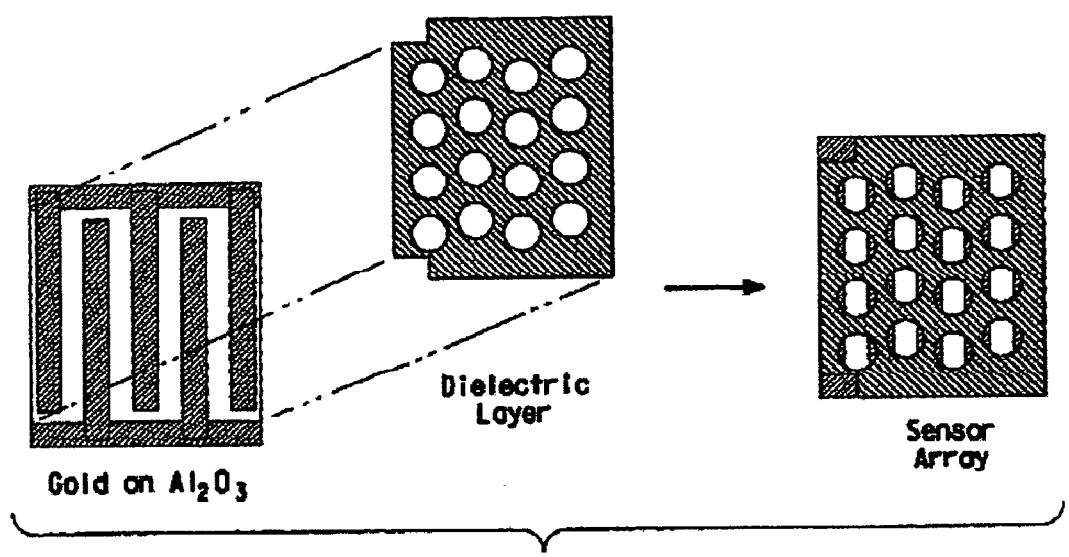
FIG. 3 is a schematic diagram of the pattern of interdigitated electrodes overlaid with the dielectric overlayer, forming sixteen blank wells of the chemical sensor array of the system shown in FIG. 1.
Figure 4A:
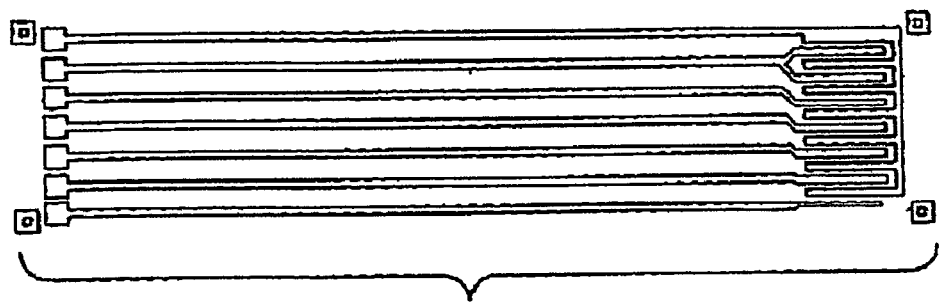
FIGS. 4A-4C depict the electrode pattern, dielectric pattern, and sensor material pattern used in preparing array chips for measurement in the chemical sensor array of the system shown in FIG. 1.
Figure 4B:
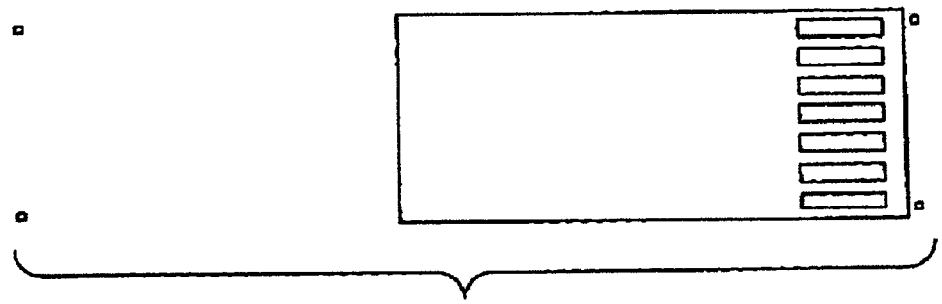
Figure 4C:
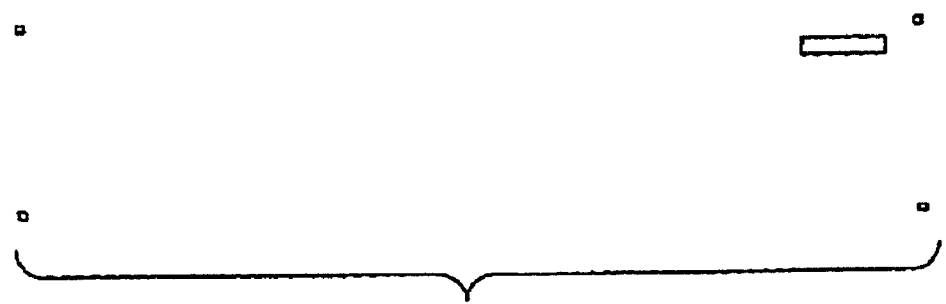

Techniques for screen-printing substrates with the electrodes and chemo-electro-active materials are illustrated in FIGS. 3 and 4A-4C. FIG. 3 depicts a method of using interdigitated electrodes overlaid with dielectric material, forming blank wells into which the chemo-electro-active materials can be deposited. FIGS. 4A-4C depict an electrode screen pattern for an array of 6 materials, which is printed on both sides of the substrate to provide for a 12-material array chip.

Two of the electrodes are in parallel so it holds only 6 unique materials. Counting down from the top of the array shown in FIGS. 4A-4C, the top two materials can only be accessed simultaneously by the split electrode with which they have shared contact (FIG. 4A). Below that is the screen pattern for the dielectric material, which is screen printed on top of the electrodes on both sides of the substrate to prevent the material from being fouled by contact with the gas mixture, such as a deposit of soot that could cause a short (FIG. 4B). Below that is the screen pattern for the actual sensor materials (FIG. 4C). This is printed in the holes in the dielectric on top of the electrodes. When more than one material is used in the array, the individual materials are printed one at a time.

An electrical response is determined for each chemo-electro-active material upon exposure of the array to a gas mixture, and means for determining the response include conductors interconnecting the sensor materials. The conductors are in turn connected to electrical input and output circuitry (detecting circuitry 200), including data acquisition and manipulation devices (analytical device 300) as appropriate to measure and record a response exhibited by a sensor material in the form of an electrical signal. The value of a response, such as a measurement related to resistance, may be indicated by the size of the signal. One or more signals may be generated by an array of sensors as to each analyte component in the mixture, whether the analyte is one or more individual gases and/or one or more subgroups of gases.

An electrical response is determined for each individual chemo-electro-active material separately from that of each of the other chemo-electro-active materials. This can be accomplished by accessing each chemo-electro-active material with an electric current sequentially, using a multiplexer to provide signals differentiated between one material and another in, for example, the time domain or frequency domain. It is consequently preferred that no chemo-electro-active material be joined in a series circuit with any other such material. One electrode, by which a current is passed to a chemo-electro-active material, can nevertheless be laid out to have contact with more than one material. An electrode may have contact with all, fewer than all, of the chemo-electro-active materials in an array. For example, if an array has 12 chemo-electro-active materials, an electrode may have contact with each member of a group of 2, 3, 4, 5 or 6 (or, optionally, more in each instance) of the chemo-electro-active materials. The electrode will preferably be laid out to permit an electrical current to be passed to each member of such group of chemo-electro-active materials sequentially.

A conductor such as a printed circuit may be used to connect a voltage source to a sensor material, and, when a voltage is applied across the sensor material, a corresponding current is created through the material. Although the voltage may be AC or DC, the magnitude of the voltage will typically be held constant. In one embodiment, however, an excitation voltage may be provided to each sensor in the form of a short pulse, the pulse being applied for less than 10% of the measurement time for each sensor. The resulting current is proportional to both the applied voltage and the resistance of the sensor material. A response of the material in the form of either the current, voltage, or resistance may be determined, and means for doing so include commercial analog circuit components such as precision resistors, filtering capacitors and operational amplifiers (such as a OPA4340). As voltage, current, and resistance is each a known function of the other two electrical properties, a known quantity for one property may be readily converted to that of another.

Resistance may be determined, for example, in connection with the digitization of an electrical response. Means for digitizing an electrical response include an analog to digital (A/D) converter, as known in the art, and may include, for example, electrical components and circuitry (e.g., detecting circuitry 200 described below) that involve the operation of a comparator. An electrical response in the form of a voltage signal, derived as described above as a result of applying a voltage across a sensor material, may be used as an input to a comparator section (such as a LM339). The other input to the comparator may be driven by a linear ramp produced by charging a capacitor using a constant current source configured from an operational amplifier (such as a LT1014) and an external transistor (such as a PN2007a). The ramp may be controlled and monitored by a microcomputer (such as a T89C51CC01). A second comparator section may be also driven by the ramp voltage, but may be compared to a precise reference voltage. The microcomputer captures the length of time from the start of the ramp to the activation of the comparators to generate a signal based on the counted time.

The resistance of the sensor material is then calculated, or quantified as a value, by a microcomputer (e.g., analytical device 300 discussed below) from the ratio of the time signal derived from the voltage output of the material to a time signal corresponding to a known look-up voltage and, ultimately, to the resistance that is a function of the look-up voltage. A microprocessor chip, such as a T89C51CC01, can be used for this function. The microprocessor chip may also serve as means for determining a change in the resistance of a sensor material by comparing a resistance, determined as above, to a previously determined value of the resistance.

Electrical properties such as impedance or capacitance may be determined, for example, by the use of circuitry components such as an impedance meter, a capacitance meter or inductance meter.

Means for digitizing the temperature of an array of chemo-electro-active materials can include, for example, components as described above that convert a signal representative of a physical property, state, or condition of a temperature measuring device to a signal based on counted time.

In one embodiment, analysis of a multi-component gas mixture is complete upon the generation of an electrical response, such as resistance, in the manner described above. As a measurement of resistance exhibited by a sensor material upon exposure to a gas mixture is a function of the partial pressure within the mixture of one or more component gases, the measured resistance provides useful information about the composition of the gas mixture. The information may, for example, indicate the presence or absence within the mixture of a particular gas or subgroup of gases. In other embodiments, however, it may be preferred to manipulate, or further manipulate, an electrical response in the manner necessary to obtain information concerning the relative concentration within the mixture of one or more particular component gases or subgroups of gases, or to calculate the actual concentration within the mixture of one or more component gases or subgroups.

Means for obtaining information concerning the relative concentration within the mixture of one or more individual component gases and/or one or more subgroups of gases, or for detecting the presence of, or calculating the actual concentration of, one or more individual component gases and/or subgroups within the mixture, may include analytical device 300 (discussed in detail below) that incorporates either a PLS (Partial Least Squares) model, a back-propagation neural network model, or a combination of the two, along with signal preprocessing and output post-processing. Signal preprocessing includes, but is not limited to, such operations as principle component analyses, simple linear transformations and scaling, logarithmic and natural logarithmic transformations, differences of raw signal values (e.g., resistances), and differences of logarithmic values. The analytical device 300 contains a model whose parameters have been previously determined, and that empirically models the relationship between the preprocessed input signal and information related to the gas concentration of the species of interest. Output post-processing includes, but is not limited to, all of the operations listed above for preprocessing, as well as their inverse operations.

The model is constructed using equations in which constants, coefficients or other factors are derived from predetermined values characteristic of a precisely measured electrical response of an individual sensor material to a particular individual gas or subgroup expected to be present as a component in the mixture to be analyzed. The equations may be constructed in any manner that takes temperature into account as a value separate and apart from the electrical responses exhibited by the sensor materials upon exposure to a gas mixture. Each individual sensor material in the array differs from each of the other sensors in its response to at least one of the component gases or subgroups in the mixture, and these different responses of each of the sensors is determined and used to construct the equations used in the model.

The analyte gas(es) contained in the mixture to which the chemo-electro-active material will be exposed can be a single gas, a subgroup of gases together, or one or more gases or subgroups mixed with an inert gas such as nitrogen. Particular gases of interest are donor and acceptor gases. These are gases that either donate electrons to the semiconducting material, such as carbon monoxide, $H_2S$ and hydrocarbons, or accept electrons from the semiconducting material, such as $O_2$, nitrogen oxides (commonly depicted as $NO_x$), and halogens. When exposed to a donor gas, an n-type semiconducting material will have a decrease in electrical resistance, increasing the current, and it, therefore, will show an increase in temperature due to $I^2R$ heating. When exposed to an acceptor gas, an n-type semiconducting material will have an increase in electrical resistance, decreasing the current, and therefore will show a decrease in temperature due to $I^2R$ heating. The opposite occurs in each instance with p-type semiconducting materials.

The geometry of a sensor material as fabricated in an array, including such characteristics as its thickness, selection of a compound or composition for use as the sensor, and the voltage applied across the array, can vary depending on the sensitivity required. The sensor materials are preferably connected in parallel in a circuit to which a voltage of about 1 to about 20, preferably about 1 to about 12 volts is applied across the sensor materials. When performing an analysis of a multi-component gas mixture, it is preferred that each chemo-electro-active sensor material in the array exhibit a different electrical response characteristic than each of the other chemo-electro-active materials in the array upon exposure to the mixture containing one or more analyte gases.

As noted, the types of electrical response characteristics that may be measured include AC impedance or resistance, capacitance, voltage, current or DC resistance. It is preferred to use resistance as the electric response characteristic of a sensor material that is measured to perform analysis of a gas mixture and/or a component therein. For example, a suitable sensor material may be that which, when at a temperature of about 400° C. or above and which has a resistance with a suitable electrode length and separation, has a resistance of at least about 100 ohm, and preferably at least about 1,000 ohm, and yet no more than about $10^6$ ohm, and preferably no more than about $10^5$ ohm. Such a sensor material may also be characterized as that which exhibits, preferably at a temperature of about 400° C. or above, upon exposure to a gas mixture, a change in resistance of at least about 0.1 percent, and preferably at least about 10 percent, as compared to the resistance in the absence of exposure.

Regardless of the type of response characteristic that is measured for the purpose of analyzing a mixture and/or a gaseous component of interest therein, it is desirable that a sensor material be utilized for which a quantified value of that response characteristic is stable over an extended period of time. When the sensor material is exposed to a mixture containing the analyte, the concentration of the analyte being a function of the composition of the particular gas mixture in which it is contained, the value of the response of the sensor material will preferably remain constant or vary to only a small extent during exposure to the mixture over an extended period of time at a constant temperature. For example, the value of the response, if it varies, will vary by no more than about twenty percent, preferably no more than about ten percent, more preferably no more than about five percent, and most preferably no more than about one percent over a period of at least about 1 minute, or preferably a period of hours such as at least about 1 hour, preferably at least about 10 hours, more preferably at least about 100 hours, and most preferably at least about 1000 hours. One of the advantages of the types of sensor materials described above is that they are characterized by this kind of stability of response.

In applications in which the gas mixture is above about 400° C., the temperature of the sensor materials and the array may be determined substantially only, and preferably is determined solely, by the temperature of the gas mixture in which a gaseous analyst is contained. This is typically a variable temperature. When higher-temperature gases are being analyzed, it may be desirable to provide a heater with the array to bring the sensor materials quickly to a minimum temperature. The temperature of the sensor materials thus rises or falls to the same extent that the temperature of the surrounding environment does. The temperature of the surrounding environment, and thus the sensors and the array, is typically determined by (or results from) substantially only the temperature of the gas mixture to which the array is exposed.

In applications in which the gas mixture is below about 400° C., it may be preferred to maintain the sensor materials and the array at a preselected temperature of about 400° C. or above. This preselected temperature may be substantially constant, or preferably is constant. The preselected temperature may also be about 500° C. or above, about 600° C. or above, or about 700° C. or above. This may be conveniently done with a heater incorporated with the array, in a manner as known in the art. The temperature of the gas mixture may also be below about 300° C., below about 200° C., or below about 100° C.

A change of temperature in the array may be indicated by a change in the quantified value of an electrical response characteristic, resistance for example, of a sensor material. At a constant partial pressure in the mixture of a gas of interest, the value of an electrical response characteristic of a sensor material may vary with a change in temperature of the array, and thus the material. This change in the value of an electrical response characteristic may be measured for the purpose of determining or measuring the extent of change of, and thus a value for, temperature. It is not required, but is preferred, that this measurement of temperature be made independently of information related to the compositional content of a gas mixture. This can be done by not using sensors that provide compositional information for the additional purpose of determining temperature, and, optionally, by connecting the temperature measuring device in parallel circuitry with the sensor materials, rather than in series. Means for measuring temperature include a thermocouple, a thermistor, or a pyrometer incorporated with an array of sensors. If the temperature determining device is a thermistor, which is typically a material that is not responsive to an analyte gas, the thermistor is preferably made from a different material than the material from which any of the gas sensors is made. Regardless of the method by which temperature or change in temperature is determined, a temperature value or a quantified change in temperature is a desirable input, preferably in digitized form, from which an analysis of a mixture of gases and/or a component therein may be performed.

In the system and method of this invention, unlike various prior-art technologies, there is no need to separate the component gases of a mixture for purposes of performing an analysis, such as by a membrane or electrolytic cell. There is also no need when performing an analysis by means of this invention to employ a reference gas, such as for the purpose of bringing a response or analytical result back to a base line value. With the exception of preliminary testing, during which a standardized response value to be assigned to the exposure of each individual sensor material to each individual analyte gas is determined, the sensor materials are exposed only to the mixture in which an analyte gas and/or subgroup is contained. The sensor materials are not exposed to any other gas to obtain response values for comparison to those obtained from exposure to the mixture containing an analyte. The analysis of the mixture is, therefore, performed only from the electrical responses obtained upon exposure of the chemo-electro-active materials to the mixture containing the analyte. No information about an analyte gas and/or subgroup is inferred by exposure of the sensor materials to any gas other than the analyte itself as contained within the mixture.

This invention therefore provides systems and methods for directly sensing the presence and/or concentration of one or more gases in an multi-component gas system, comprising an array of at least two chemo-electro-active materials chosen to detect the gases in a multi-component gas stream. The multi-component gas system can be at essentially any temperature that is not so low or so high that the sensor materials are degraded or the sensor apparatus otherwise malfunctions. In one embodiment, the gas system may be at a lower temperature such as room temperature (about 25° C.) or elsewhere in the range of about 0° C. to less than about 100° C., whereas in another embodiment the gas mixture may at a higher temperature such as in the range of about 400° C. to about 1000° C.

The invention is applicable to gas mixtures that may be at higher temperatures—gases, for example, as found in combustion streams such as the exhaust or emission of an automobile, diesel engine, or home heating systems. The invention is also applicable, however, to gas mixtures derived from other sources, such as in manufacturing processes, waste streams, and environmental monitoring; or in systems in which odor detection is important and/or that are at lower temperature, such as in the medical, agricultural or food and beverage industries. An array of chemo-electro-active materials could be used, for example, to supplement the results of, or calibrate, a gas chromatograph. The gas mixture may therefore have a temperature that is about 100° C. or more, about 200° C. or more, about 300° C. or more, about 400° C. or more, about 500° C. or more, about 600° C. or more, about 700° C. or more, or about 800° C. or more, and yet is less than about 1000° C., is less than about 900° C., is less than about 800° C., is less than about 700° C., is less than about 600° C., is less than about 500° C., is less than about 400° C., is less than about 300° C., is less than about 200° C., or is less than about 100° C.

This invention also provides a chemical sensor for directly sensing the presence and/or concentration of one or more gases in a multi-component gas system, including a substrate, an array of at least two chemo-electro-active materials chosen to detect one or more predetermined gases in a multi-component gas stream, and a means to detect changes in electrical properties in each of the chemo-electro-active materials present upon exposure to the gas system.

A sensor that has the needed sensitivity, and that can operate to generate the types of analytical measurements and results described above, is obtained by selection of appropriate compositions of materials from which the sensor is made. Various suitable compositions of materials for this purpose are described above. The number of sensors in the array is typically greater than or equal to the number of individual gas components to be analyzed in the mixture.

The gas mixture to be analyzed may be emitted by a process, or may be a product of a chemical reaction that is transmitted to a device. In such instance, the invention may further include means for utilizing the electrical response of an array, and optionally a temperature measurement, for the purpose of controlling the process or the device.

Means for utilizing an electrical response of a sensor material, and optionally a temperature measurement, for controlling a process or device include a decision making routine to control, for example, the chemical reaction of combustion that occurs in an internal combustion engine, or to control the engine itself, or components or equipment associated therewith.

Combustion is a process in which the chemical reaction of the oxidation of a hydrocarbon fuel occurs in the cylinder of an engine. An engine is a device to which a result of that chemical reaction is transmitted, the result being the force generated by the combustion reaction to the work necessary to move the piston in the cylinder. Another example of a process that emits a multi-component mixture of gases is the chemical reaction that occurs in a fuel cell, and other examples of a device to which a product of a chemical reaction is transmitted is a boiler, such as used in a furnace or for power generation, or a scrubber in a stack to which waste gases are transmitted for pollution abatement treatment.

In the case of an engine, to control the process of combustion or the operation of the engine itself, a microcomputer (such as a T89C51CC01 from Atmel Corporation of San Jose, Calif.) may perform a multitude of decision-making routines about various parameters of the process of combustion or about operating characteristics of the engine. The microcomputer gathers information about the compositional content of the engine exhaust, and does so by obtaining the responses of an array of chemo-electro-active materials that have been exposed to the stream of exhaust, and optionally obtains a temperature measurement. The information is temporarily stored in a random access memory, and the microcomputer then applies one or more decision-making routines to the information.

A decision-making routine (e.g., analytical device 300) may utilize one or more algorithms and/or mathematical operations to manipulate the acquired information to generate a decision in the form of a value that is equivalent to a desired state or condition that should be possessed by a particular parameter of the process, or by an operating characteristic of the device. Based on the result of a decision-making routine, instructions are given by or are controlled by the microcomputer that cause an adjustment in the state or condition of a parameter of the process or an operating characteristic of the device. In the case of the process embodied by the chemical reaction of combustion, the process can be controlled by adjusting a parameter of the reaction, such as the relative amount of the reactants fed thereto. The flow of fuel or air to the cylinder, for example, can be increased or decreased. In the case of the engine itself, being a device to which a result of the reaction of combustion is transmitted, control can be accomplished by adjusting an operating characteristic of the engine such as torque or engine speed.

An internal combustion engine and the associated components and equipment, controlled by the systems and methods of this invention, can be used for many different purposes including, for example, in any type of vehicle for transportation or recreation such as a car, truck, bus, locomotive, aircraft, spacecraft, boat, jet ski, all-terrain vehicle, or snowmobile; or in equipment for construction, maintenance or industrial operations such as pumps, lifts, hoists, cranes, generators, or equipment for demolition, earth moving, digging, drilling, mining or grounds keeping.

The examples set forth in U.S. patent application Ser. Nos. 10/117,472 and 09/977,791 are not repeated herein, but are incorporated by reference herein.

B. The Detecting Circuitry

As noted above, in accordance with the present invention, there may be provided chemical sensors comprised of materials whose impedance changes when exposed to certain gases. In order to avoid polarization of the impedance detecting electrodes with DC measurements, AC measurements are preferred. Accordingly, several exemplary detecting circuits 200 according to the present invention for measuring such AC impedances will now be described. Some of the circuit concepts are found, for example, in U.S. Pat. No. 4,554,639, which is owned by the assignee hereof and which is incorporated herein by reference.

The sensor array 100 is based on the variation of resistance elements in response to known contaminants. The measurement of contamination is complicated by the variation in resistance due primarily to temperature changes in the environment of the sensor array 100. The presumption is that the sensor resistor elements are a function of temperature, T, and concentration, C, such that $R(T,C)$ is of the form $R(T)K(C)$. Important sensor element characteristics include: (1) the dynamic range of resistance values to be measured; (2) the expected sensitivity to the measured contamination; (3) the time response; and (4) the noise characteristics.

The system requirements, in conjunction with the resistor element characteristics, that dictate a measurement approach include: (1) measurement accuracy; (2) measurement resolution; (3) update rate; and (4) calculation complexity. Accuracy and resolution interact with the dynamic range and sensitivity. Being able to measure the resistance to 0.1% accuracy does not ensure that the concentration can be measured to the same precision. If the full-scale change in resistance is only 10% of the nominal resistance, the concentration reading is accurate to only 1% of the full-scale value.

The time response also affects the update rate. The Nyquist criteria states that the sample rate must be greater than twice the highest frequency response. Assuming a sensor time constant of one second, the highest expected frequency is $2\pi$ Hz and the sample rate must be $4\pi$ Hz. Sampling faster than this rate may be necessary to allow digital filtering to remove noise.

Resolution is a different concept than accuracy. An analog-to-digital converter ("ADC") may have a resolution of 12 bits (1 in 4096) and still only have an accuracy of only 0.1%. The 12 bits, even if the ADC is accurate and linear to ±½ bit, can result in much lower resolution of the measured value depending on the full-scale change.

Each sensor will also have different calibration constants that must be available to the microcontroller. It would be desirable to have the constants associated with the sensor if the sensor and electronics have to be separated. The ideal device for constant memory is a serial EEPROM. For a normal automotive temperature range (−40° C. to 125° C.), these devices are inexpensive, but so far, none have been found that can withstand the high temperature environment expected in the sensor itself. With a separate sensor and electronics unit, it is possible to integrate the memory chip in the connector between the two units.

Figure 5:
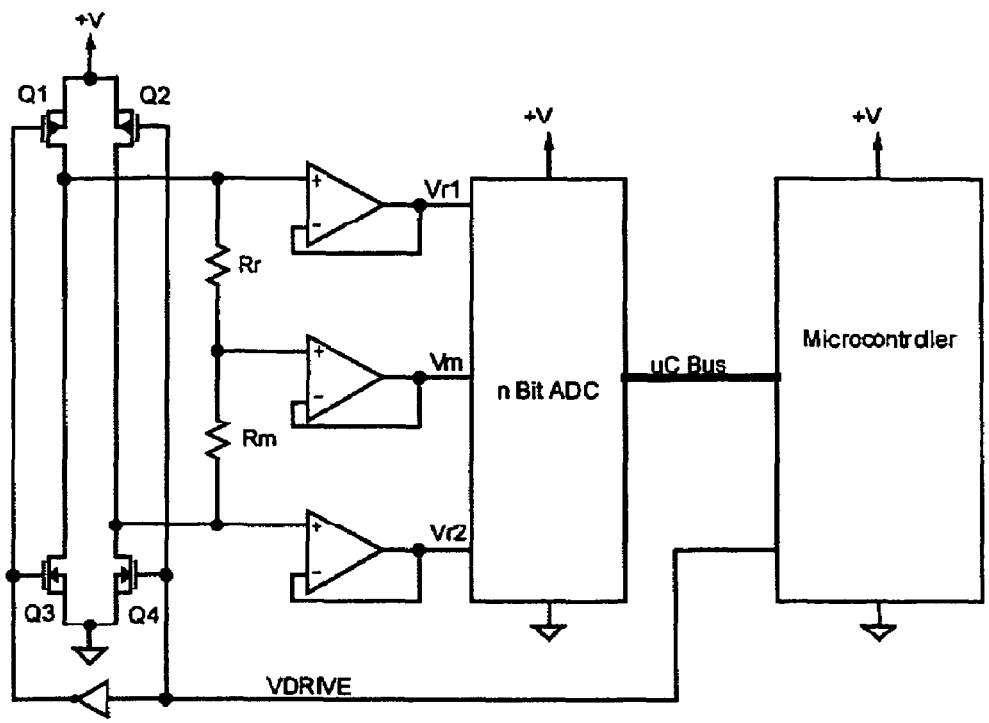
FIG. 5 is an electrical circuit schematic showing a linear resistance ratio measurement approach.

The fact that the sensor resistor is to be driven AC complicates the measurement. A simple approach is to measure a resistor as a ratio against a reference resistor, as shown in FIG. 5. The technique requires two readings, first with the VDRIVE signal low and then with the VDRIVE signal high, wherein the VDRIVE signal is the measurement excitation signal applied to the resistors to be measured. In both cases the limits, Vr1 and Vr2, as well as, the divider point, Vm, are measured. These two measurements give the following result:

$$V1 = \frac{Rm}{Rm + Rr},$$

and $$V2 = \frac{Rr}{Rm + Rr}.$$

Thus, $$Rm = Rr \cdot \frac{V1}{V2}.$$

The conductance, Gm, is simply an inversion of this equation.

The purpose of measuring the limits is to allow the readings to be corrected for voltage drops expected in the measurement technique. Since the measurement is made against a reference resistor, Rr, it must be stable and accurate. For this reason, it would be part of the measurement circuit, not in the sensor itself.

A virtue of this approach is that no absolute reference is needed in the measurement circuitry. Further, resolution and accuracy are determined by the minimum number of bits used. For example, with a 12-bit ADC and a minimum reading of 1000, the measurement of the resistor value is resolvable to 10 bits or 0.1%. This corresponds to a total change in resistance value of 3 to 1. For a 1% resolution, the range is approximately 31 to 1. The exact dynamic range, D(n,m), for an ADC with n bits resolution and an estimate resolution of m bits, is given by, $D(n,m)=2^{n-m}-1$, and the resolution of the estimate of resistance ratio, E(m), is given by, $E(m)=2^m$.

The calculation of resistance in this example requires that the readings be corrected for the offsets of the drive level limits, and then performing a division. The ratio of Rm/Rr must be such that the expected range of change in Rm does not exceed the dynamic range limits. This approach is adaptable to reading multiple sensor resistors simultaneously by adding a buffer amplifier and local reference resistor for each sensor resistor. For a six-sensor system, an eight-channel ADC would be adequate to measure all sensors simultaneously. To measure more sensors would require multiplexing the inputs to the ADC. It is possible to make readings on all 12 channels in each cycle of a drive frequency of 100 Hz.

Figure 6:
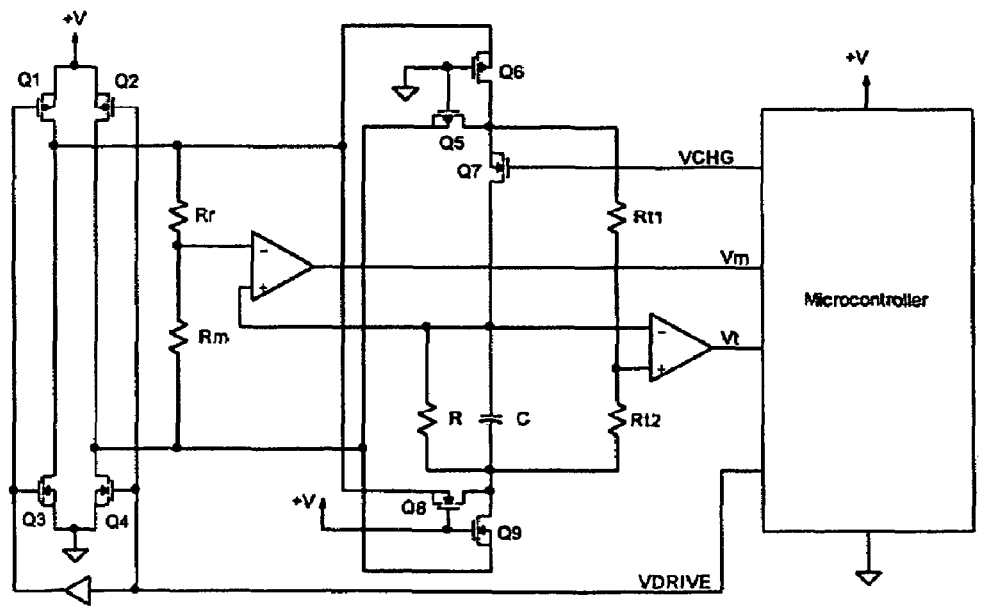
FIG. 6 is an electrical circuit schematic showing a measurement approach that uses a timing technique to produce a log measurement of an unknown resistance.

A variation in the above approach uses a timing technique to produce a log measurement of the unknown resistance. This approach is adaptable to direct interface to a microcontroller and requires no ADC as shown in FIG. 6. The microcontroller, via VDRIVE, controls field-effect transistors ("FETs"), Q1 to Q4, to alternate the direction of current flow through Rm and Rr. FETs, Q5, Q6, Q8 and Q9, undo the effects of FETs, Q1 to Q4, to maintain a unidirectional reference to the timing circuit. After setting the state of current flow, the microcontroller enables Q7 to charge capacitor C to the upper rail. The reference to the timing comparator, as established by Rt1 and Rt2, allows the measurement of the time constant, $\tau$, of R and C. A timer is started when Q7 is turned off and the time that Vt and Vm are high is measured. On the next phase of VDRIVE, the process is repeated.

The first time measurement, t1, corresponds to voltage V1, such that, $$V1 = V \cdot e^{\frac{-t1}{\tau}} = V \cdot \frac{Rm}{Rm + Rr}.$$

The second time measurement, t2, corresponds to V2, $$\text{or } V2 = V \cdot e^{\frac{-t2}{\tau}} = V \cdot \frac{Rr}{Rm + Rr}.$$

Simplifying and solving for the natural log of Rm gives, $$\ln(Rm) = \frac{t1 - t2}{\tau} + \ln(Rr).$$

Note that the time, $\tau$, is measured on both halves of the cycle so minor variations in the values of timing components, R and C, are not significant. The measurement is actually based on the ratio of timing resistors, Rt1 and Rt2, and the stability and accuracy of the local reference resistor, Rr.

FIGS. 7 and 8 present timing characteristics normalized to $\tau$ as a function of the dynamic range of Rm, Dr. FIG. 7 gives the total time, t, for the measurement based on the equation, $t(Dr)=\tau\cdot\ln(\sqrt{Dr}+1)$. FIG. 8 gives the time difference, $\Delta t$, based on the equation, $\Delta t(Dr)=\tau\cdot\ln(\sqrt{Dr})$.

The virtue of measuring the log of Rm is that accuracy of the measurement is a percent of the reading rather than a percent of the full-scale. FIG. 9 shows the resolutions, in percent, as a function of the precision of the $\tau$ measurement, in counts as given by, $$Res(Dr, N) = 100 \cdot (10^{\frac{\log(Dr)}{N}} - 1).$$

Five curves are given for dynamic ranges of 3, 10, 100, 1,000, and 10,000.

The penalty paid for added accuracy and wider dynamic range is measurement time. The primary factor impacting the measurement time is the maximum counting rate of the microcontroller. Several microcontrollers incorporate PCAs (programmable counter arrays) intended for high-speed timing functions. The microcontrollers can count at rates of ¼ the crystal frequency. For a practical 16 MHz crystal, the time resolution is thus 250 ns. From FIG. 9, for a dynamic range of 100 and a resolution of 0.1%, the value of $\tau$ required is approximately 1.25 ms. From FIG. 6 the required maximum time for the measurement is 2.4 times $\tau$, or 3 ms.

The simplest microcontroller that could be used to implement this approach and meet the automotive temperature environment (125° C.) is the 89C51CC01 series microcontroller available from Atmel Corporation. This microcontroller has a 5-channel PCA, which would allow simultaneous measurement of four sensor resistors. To measure more resistors requires multiple sample periods. This microcontroller has a built-in CAN interface. Each unknown resistor to be measured requires a comparator and local reference resistor.

Figure 10:
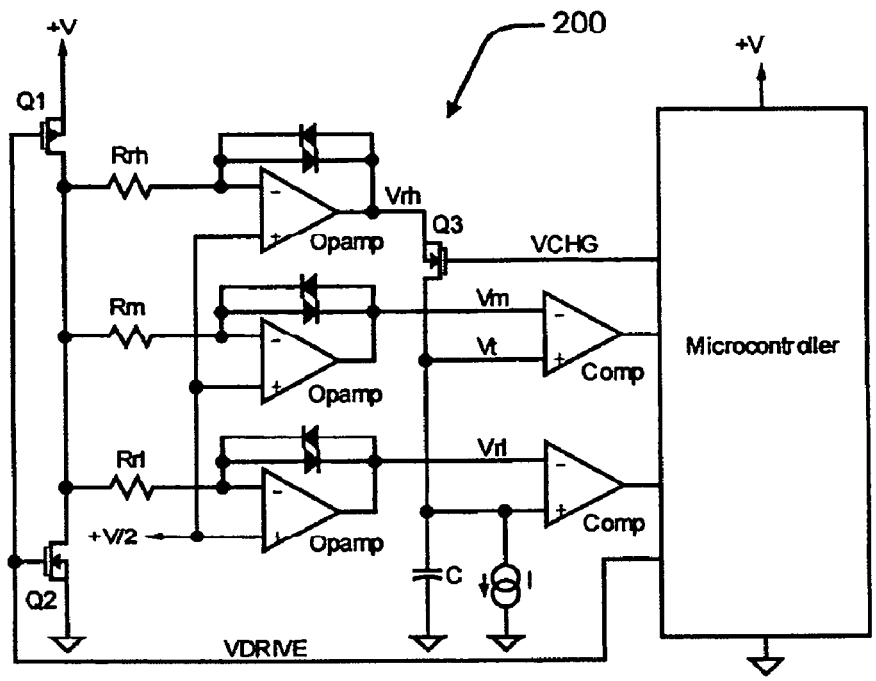
FIG. 10 is an electrical circuit schematic of an analog logged measurement in accordance with the present invention and for use in the detecting circuitry of the system shown in FIG. 1.

One measuring circuit in accordance with the detecting circuitry 200 of the present invention is shown in FIG. 10. In this circuit, Rm represents a material whose AC impedance will be determined. The material receives a drive frequency that is preferably 100 Hz.

As known in the art, the current and voltage relationship in a diode follows the equation, $$Vd = \frac{k \cdot T}{q} \cdot \ln\left(\frac{I}{I_o}\right) + V_o(I_o, T),$$

where, Vd is the voltage across the diode, I is the current through the diode, k is Boltzmann's Constant, T is the absolute temperature, q is the electron charge, $I_o$ is a reference current, and $V_o(I_o,T)$ is a voltage dependent on $I_o$ and T.

At normal room temperature, a change in current by a factor of 10 causes a change in the diode voltage Vd of 60 mV. Measurement of the voltage is complicated by the temperature sensitivity of both the measured value and the offset voltage $V_o$. However, assuming matched diodes, which are inherent in an integrated circuit, these unknowns can be eliminated by using similar circuits with known currents as in the present invention.

In the circuit of FIG. 10 measurements are only made while VDRIVE is high and the current is being drawn through FET Q2. On the opposite phase of VDRIVE, when FET Q1 is active, balanced current is drawn. After setting VDRIVE high, FET Q3 is activated to charge capacitor, C, to the upper reference voltage, Vrh, as determined by resistor, Rrh. Q3 is then turned off and C discharges linearly through the constant current source, I. Using its programmable counter arrays (PCA's), the microcontroller measures the times tm and tr for the timing voltage Vt to pass voltages Vm and Vr1. Vm is thus, $$Vm = \frac{tr - tm}{tr} \cdot (Vrh - Vrl) + Vrl.$$

From the diode equation, the voltages Vm, Vrh, and Vrl are given by, $$Vm = \frac{k \cdot T}{q} \cdot \ln\left(\frac{V}{Rm \cdot I_o}\right) + V_o(I_o, T),$$

$$Vrh = \frac{k \cdot T}{q} \cdot \ln\left(\frac{V}{Rrh \cdot I_o}\right) + V_o(I_o, T),$$

and $$Vrl = \frac{k \cdot T}{q} \cdot \ln\left(\frac{V}{Rrl \cdot I_o}\right) + V_o(I_o, T).$$

Substituting for the voltages, and solving for ln(Rm) gives, $$\ln(Rm) = \ln(Rrh) + \frac{tm}{tr} \cdot \ln\left(\frac{Rrl}{Rrh}\right).$$

Because all the unknowns normalize out, the measurement of ln(Rm) is only a function of the values of resistors Rrl and Rrh. If more than one Rm is to be measured, an additional operational amplifier ("opamp") and diode pair must be added for each additional Rm. The outputs of the comparators can be multiplexed into the microcontroller timer inputs.

The resolution of the measurement is determined by the dynamic range Dr, the reference time tr and the counter resolution of the microcontroller. Assuming the ratio of Rrl/Rrh determines the dynamic range and a tm between zero and tr, the resolution data shown in FIG. 9 applies directly to this approach. Accordingly, for a dynamic range of 100, a resolution of 0.1%, and a microcontroller clock frequency of 16 MHz, the required time for measurement by the microcontroller is 1.25 ms.

Figure 11:
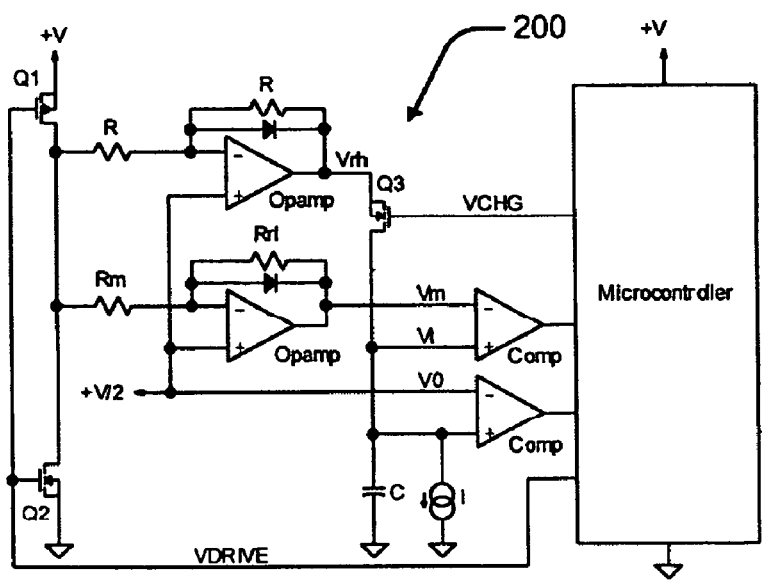
FIG. 11 is an electrical circuit schematic of a timed linear resistance measurement in accordance with the present invention and for use in the detecting circuitry of the system shown in FIG. 1.

Another variation of the approach of FIG. 10, and in accordance with the present invention, is shown in FIG. 11. Again, Rm represents a material whose AC impedance will be determined, and the material receives a drive frequency that is preferably 84 Hz. In this circuit, an operational amplifier is used to interface to Rm. The feedback resistor, Rrl, is selected to correspond to the minimum value of resistance expected in the unknown, Rm. This circuit only makes a measurement when VDRIVE is high. When VDRIVE is low, equal but opposite current is drawn through Rm. When Q2 is on, the timing capacitor, C, is charged to a reference voltage, Vrh, determined by two equal value resistors. If Rm is infinite, the measured voltage Vm is equal to V0 or +V/2. Again, the times for Vt to pass Vm and V0 are measured. The value of Rm is thus, $$Rm = \frac{Rrl}{1 - \frac{tm}{tr}}.$$

Expressing the result in terms of conductance, Gm, gives, $$Gm = Grl \cdot \left(1 - \frac{tm}{tr}\right).$$

Since this is a direct measurement of Rm, the resolution is strictly a function of the dynamic range and the timing resolution. By picking a unique reference resistor value for Rrl to go with each unknown resistor, the dynamic range and resolution of each resistor measurement path can be established independently.

Figure 12:
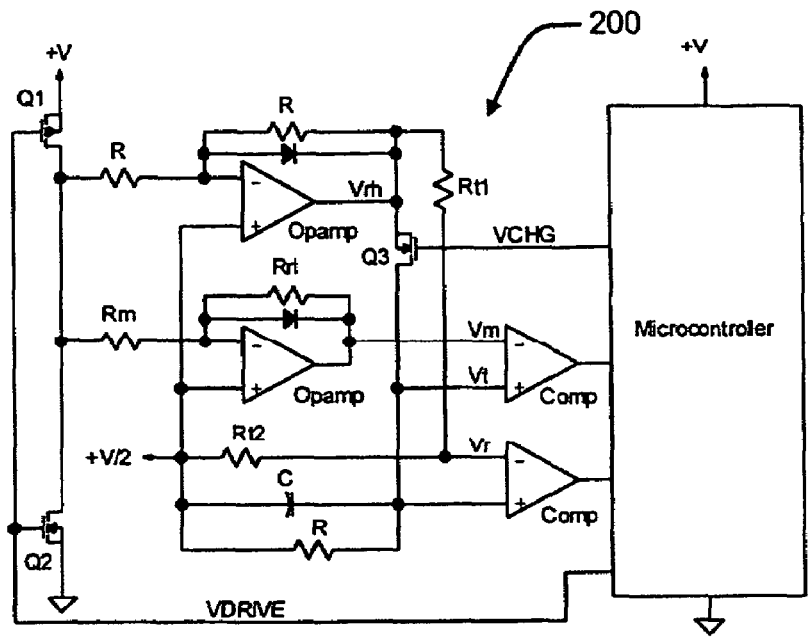
FIG. 12 is an electrical circuit schematic of a timed log measurement in accordance with the present invention and for use in the detecting circuitry of the system shown in FIG. 1.

A variation of the circuit of FIG. 11, as shown in FIG. 12, and in accordance with the present invention, results in a direct timed log measurement of the resistance of conductance. The current source of FIG. 11 is replaced with a resistor, and resistors Rt1 and Rt2 are added to establish a reference voltage, Vr. Assuming that Vr is set to be equal to that of one time constant, $\tau$, the equations for ln(Rm) and ln(Gm) are, $$\ln(Rm) = \ln(Rrl) + \frac{tm}{t\tau}, \text{ and } \ln(Gm) = \ln(Grl) - \frac{tm}{t\tau}.$$

An advantage of this circuit over the circuit of FIG. 10 is that it can be configured without the requirements of matched diodes. It can thus be implemented with off-the-shelf components.

As many as 12 resistors may need to be measured. No available microcontrollers can measure that many resistors simultaneously using the timing technique. However, it is possible to measure 12 resistors using an ADC in conjunction with a multiplexer in accordance with the present invention.

Using a timing approach, multiplexing can take place in various ways. The sensor interface circuitry can be duplicated and the outputs multiplexed at the input to the microcontroller. Multiplexer circuits at the inputs to the sensor interface circuit are also possible but not preferred.

Figure 13:
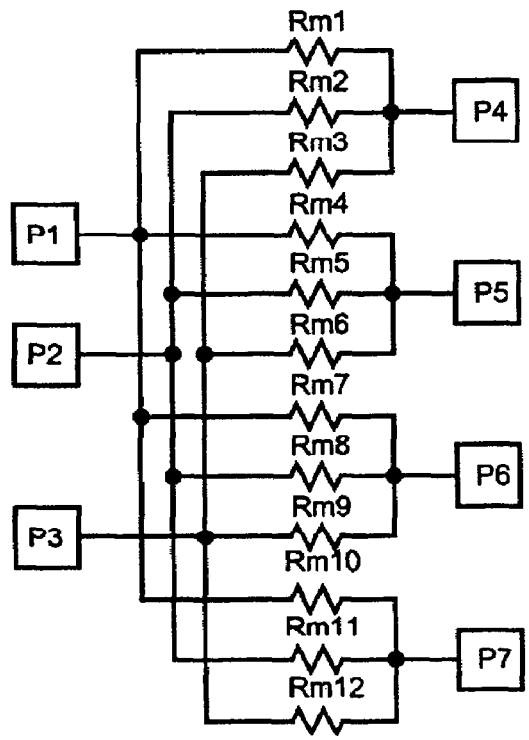
FIG. 13 is an electrical circuit schematic of a multiplexed sensor configuration in accordance with the present invention and for use in the detecting circuitry of the system shown in FIG. 1.

In circuit configurations using operational amplifiers to interface to the sensor resistors, such as those of FIGS. 10-12, a unique multiplexing technique of the present invention can be used. Assuming a 12-resistor sensor connected as shown in FIG. 13, only 7 wires need to be supplied to the sensor, rather than 13 wires. Pads, P4-P7, drive measurement interface circuits. Pads, P1-P3, are driven by separate, tri-state output circuits. By grouping sensor resistors with similar sensitivities, it is still possible to take advantage of tailoring the dynamic range and measurement resolution.

Drive multiplexing requires that transistors, Q1 and Q2, of FIGS. 10-12 be replicated for each drive path. The gates of all drive transistors must be driven independently to allow only one to be on at a time. A measurement of each resistor will require three cycles of the drive waveform. When the Rm are driven at 100 Hz, 33 measurements per second is practical and allows approximately 2.5 ms for each reading, or approximately 10,000 counts with a 16 MHz crystal.

Figure 14:
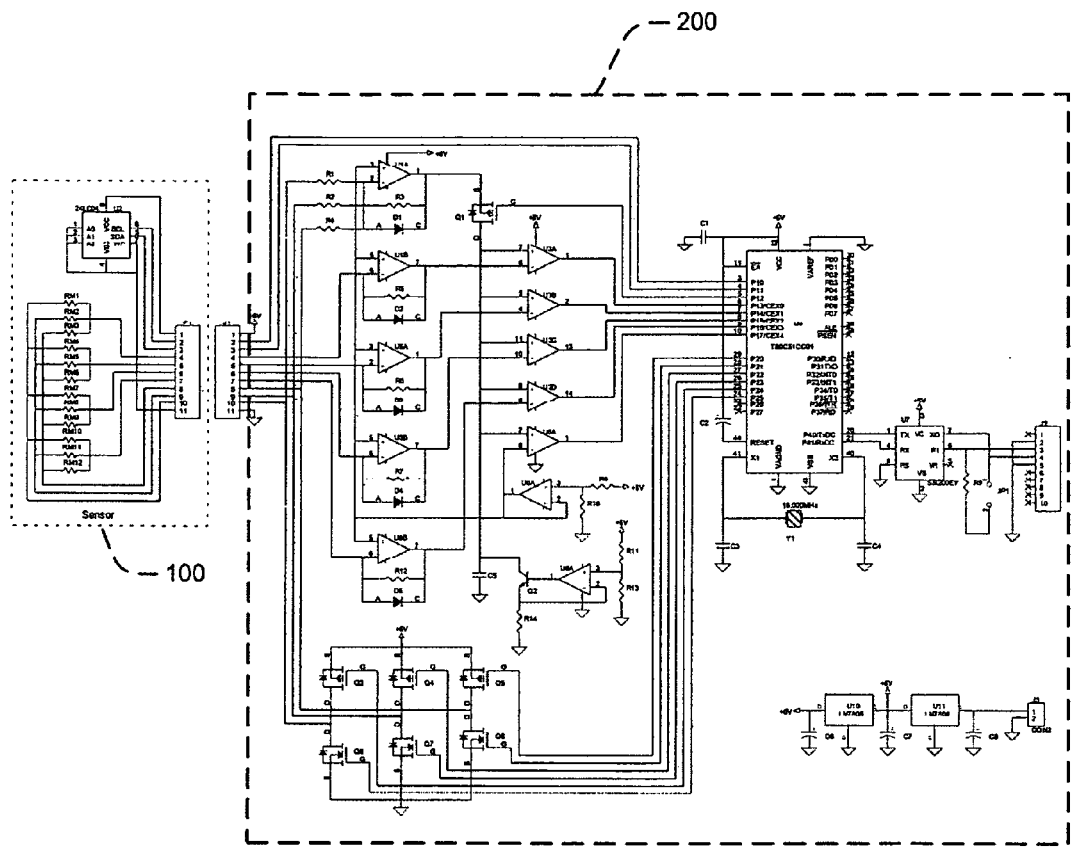
FIG. 14 is an expanded electrical circuit schematic in accordance with the present invention based on and adding additional capability to the electrical circuit shown in FIG. 11.

Shown in FIG. 14 is an expanded circuit in accordance with the present invention and based upon and adding additional capability to the circuit shown in FIG. 11. The circuit shown in FIG. 14 allows for the simulations measurement of 12 Rm. Such simultaneous measurement of 12 Rm using the timing techniques employed in the circuits of FIGS. 10 and 11 is not possible using currently-available microcontrollers. However, the circuit of FIG. 14 includes a multiplex interface, which overcomes this limitation. This multiplex interface circuit is shown in detail in FIG. 13.

For purposes of illustration, FIG. 14 shows the use of a 89C51CC01 microcontroller (available from Atmel Corporation) with five programmable counter arrays. However, other known microcontrollers may be used. FIG. 14 additionally shows a CAN interface, as is typically used in automotive applications.

All measurement techniques presented rely on local reference resistors. No absolute reference is needed for any of the circuits. Self-compensation is inherent in all the approaches. In the circuits based on timing, variations in timing component values with temperature are normalized by calibrating the timing circuit along with each measurement. Thus, the only components necessary for accuracy are the local reference resistors.

C. The Analytical Device

The apparatus and method set forth in U.S. patent application Ser. Nos. 10/117,472 and 09/977,791 generate information, via detecting circuit that needs to be computer processed to calculate the concentration or constituents of a multi-component gas system. The analytical system and method of the present invention provides the mechanisms to calculate the concentration or constituents of one or more analyte gases in the mixture of the system.

1. Hardware of the Analytical Device

Figure 15:
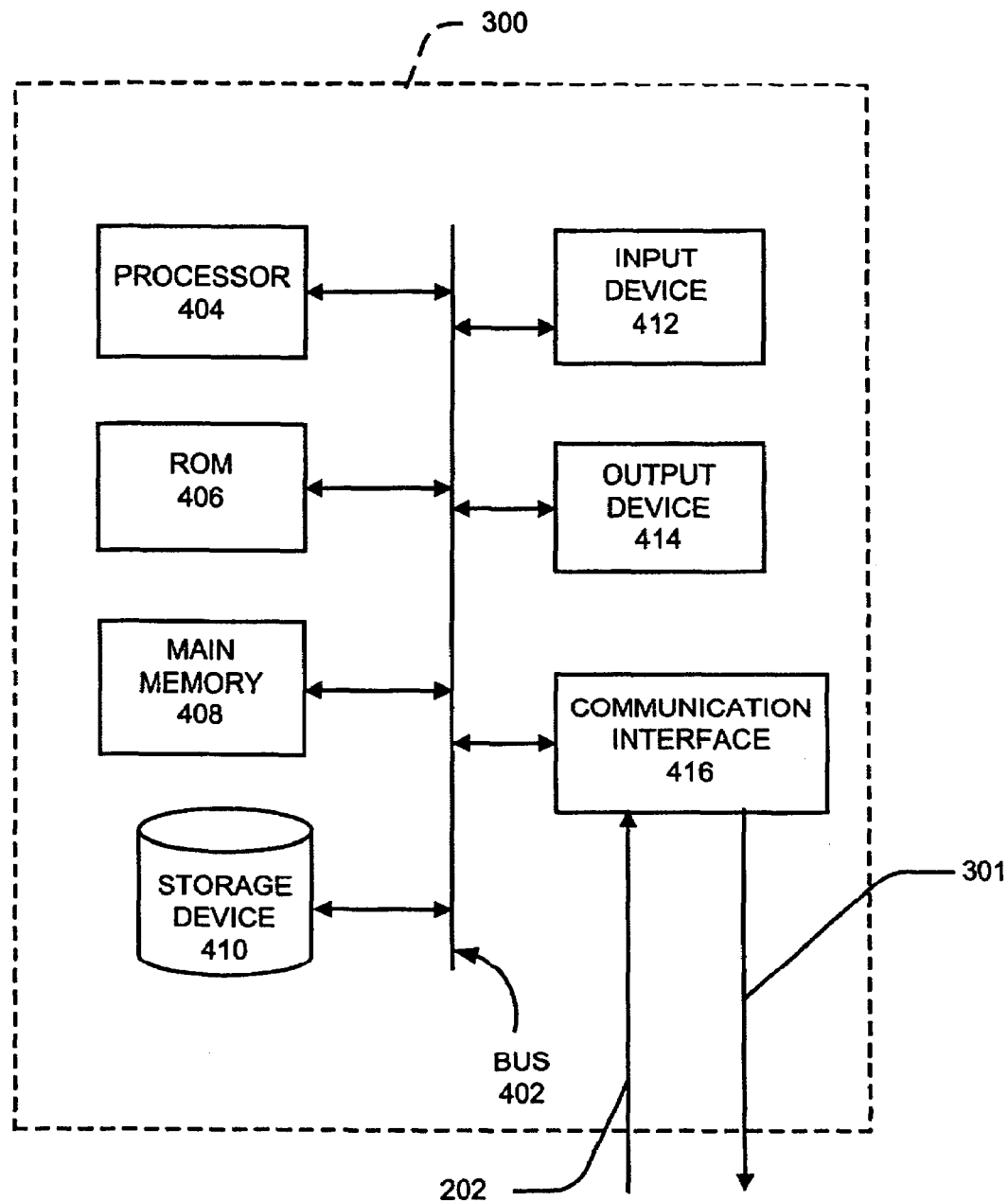
FIG. 15 is a schematic diagram showing a computing entity for use with the analytical device of the system shown in FIG. 1.

Analytical device 300 preferably comprises a conventional computing entity, or a series of connected conventional computing entities (e.g., a microcomputer such as the T89C51CC01 discussed above). As shown in FIG. 15, each computing entity may include a bus 402 interconnecting a processor 404 a read-only memory (ROM) 406, a main memory 408, a storage device 410, an input device 412, an output device 414, and a communication interface 416. Bus 402 is a network topology or circuit arrangement in which all devices are attached to a line directly and all signals pass through each of the devices. Each device has a unique identity and can recognize those signals intended for it. Processor 404 includes the logic circuitry that responds to and processes the basic instructions that drive the computer. ROM 406 includes a static memory that stores instructions and date used by processor 404.

Computer storage is the holding of data in an electromagnetic form for access by a computer processor. Main memory 408, which may be a RAM or another type of dynamic memory, makes up the primary storage of the computer. Secondary storage of the computer may comprise storage device 410, such as hard disks, tapes, diskettes, Zip drives, RAID systems, holographic storage, optical storage, CD-ROMs, magnetic tapes, and other external devices and their corresponding drives.

Input device 412 may include a keyboard, mouse, pointing device, sound device (e.g. a microphone, etc.), biometric device, or any other device providing input to the computer. Output device 414 may comprise a display, a printer, a sound device (e.g. a speaker, etc.), an electrical analog signal, or other device providing output to the computer. Communication interface 416 may include network connections, modems, or other devices used for communications with other computer systems or devices.

As will be described below, analytical device 300 consistent with the present invention may calculate the concentration or constituents of a multi-component gas system. Device 300 performs this task in response to processor 404 executing sequences of instructions contained in a computer-readable medium, such as main memory 408. A computer-readable medium may include one or more memory devices and/or carrier waves.

Execution of the sequences of instructions contained in main memory 408 causes processor 404 to perform processes that will be described later. Alternatively, hardwired circuitry may be used in place of or in combination with software instructions to implement processes consistent with the present invention. Thus, the present invention is not limited to any specific combination of hardware circuitry and software.

2. Processing by the Analytical Device

Figure 16:
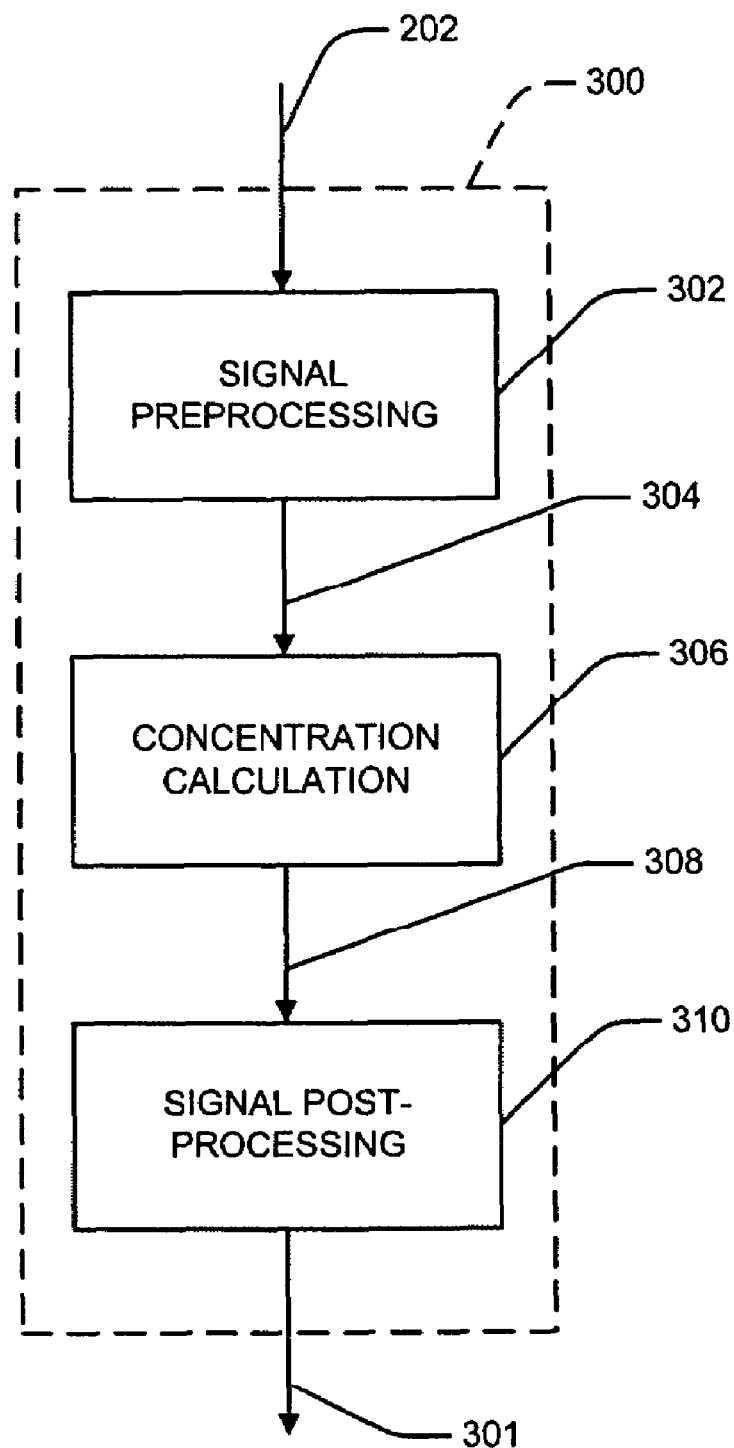
FIG. 16 is a flow chart of the processing performed by the computing entity shown in FIG. 15.

Analytical device 300 receives inputs (e.g., resistances) 202 from the chemical sensor array 100, via detecting circuitry 200, and calculates the concentrations or constituents (e.g., $NO_x$) of a multi-component gas system based upon the received inputs. The sensor array 100 provides output resistances over time that need to be correlated with the concentrations or constituents of a multi-component gas system. FIG. 16 shows the method or process for calculating the concentration or constituents of a multi-component gas system, as performed by analytical device 300. The sensor signals, data, information, resistances, etc. 202 from detecting circuitry 200 are received by analytical device 300 and need to be translated into an output of gas constituents or concentrations by analytical device 300. To accomplish this, the sensor signals 202 are first preprocessed in a signal preprocessing step 302. The preprocessed signals 302 are then provided to a concentration calculation step 306, where concentration responsive signals are calculated from stored signals and outputted as shown by reference numeral 308. The concentration responsive signals are then subjected to post-processing in a signal post-processing step 310. The signal post-processing step 310 performs post-processing on the selected data 308 and outputs the gas constituents or concentrations 301. The gas constituent or concentration information 301 may then be utilized to, for example, adjust the fuel/air mixture to optimize engine performance and eliminate unnecessary combustion waste. Each step of the process of the present invention is discussed below.

a. Signal Preprocessing

The resistance signals may be improved for subsequent concentration calculations by modification or signal preprocessing. If the resistance was measured as the absolute resistance, then it may be improved by converting it into the log as $R'=\ln(R_m)$ and $R'$ is used in subsequent concentration calculations. Another signal preprocessing approach that may be used is to normalize the resistance signal with respect to temperature through a further processing step such as $R''=R'/T(°K)$ or $R''=R_m/T(°K)$, where $R''$ is used in subsequent concentration calculations. Depending upon the concentration calculating model, other conventional preprocessing operations may be used, such as mean centering, scaling, and weighting.

b. Concentration Calculation

Many approaches exist for converting the preprocessed resistances into concentration proportional signals. Which approach is chosen depends upon the needed accuracy, computational power available, speed of processing, etc. Classical least-squares, also known as a K-matrix calibration, is one such technique. In this case, the sensor resistances, or their preprocessed analogs, can be related to the concentration of gas components by classical least-squares, in which the following assumption is made: $R=KC$, where R is the resistance matrix or the matrix of preprocessed resistances, and C is the concentration matrix. The concentration of gas components are calculated from the equation $C_{unk}=K_{cal}R_{unk}$ and $K_{cal}=[K^TK]^{-1}K^T$. K is calculated during calibration of the sensor at which time several measurements of resistances under different gas concentrations are made and then derived from the expression $K=RC^T[CC^T]^{-1}$. Similar to the classical-least squares method is the inverse least-squares method, also known as a P-matrix calibration.

There are many other approaches to converting sensor resistance arrays. Preferred among these are factor analyses such a principal component regression or partial least squares. These rely on converting observed parameters such as concentration and resistances to different frames of reference in dimensional space. By optimizing signal variance in these other dimensions and then applying, for example, classical least squares, an improvement in the quality of the relationship between resistances and gas concentrations may be obtained.

c. Signal Post-Processing

Depending upon the output device, different types of signal post-processing may be used. If the signal is to be provided to an engine computer, the gas concentration signals may be converted into analog form, with each analog signal scaled appropriately for the ECU. If the signal is to be provided to the engine computer over a digital bus, then it would be converted into the appropriate protocol.

It will be apparent to those skilled in the art that various modifications and variations can be made in the computer-implemented system and method for sensing and analyzing certain gases, including $NO_x$, hydrocarbons, carbon monoxide and oxygen in a multi-component gas system using chemical sensors and chemical sensor arrays of the present invention and in construction of this system and method without departing from the scope or spirit of the invention. Examples of which have been previously provided.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for converting the resistances of an array of N number of metal oxide sensors into digital signals, wherein the sensors respond to the concentration of gases surrounding the sensor array, comprising
    (a) an electronic excitation source that provides an excitation voltage to each sensor and to a reference resistor associated with that sensor;
    (b) an operational amplifier pair associated with each sensor/resistor pair to output to a comparator pair signals related to the resistance of the sensor and of the resistor; and
    (c) a microcontroller having multiple inputs that receives on an input pair signals that are output by a comparator pair, wherein the microcontroller measures as a digital signal the time required for each comparator to change state after a trigger signal.

2. The device of claim 1, wherein the electronic excitation device provides an excitation voltage comprising a short pulse to each sensor, the pulse being applied for less than 10% of the measurement time for each sensor.

3. The device of claim 1, wherein the electronic excitation device provides an excitation voltage comprising a constant direct current voltage.

4. The device of claim 1, wherein the resistance of each sensor is converted to a digital number representing the ratio of the sensor resistance to the resistance of the reference resistor.

5. The device of claim 1, wherein the resistance of each sensor is converted to a digital number representing the log of the ratio of the sensor resistance to the resistance of the reference resistor.

6. The device of claim 1, wherein the resistance of each sensor is converted to a digital number representing the numerical log of the sensor resistance.

7. The device of claim 1, wherein the resistance of each sensor is converted to a digital number representing the reciprocal of the sensor resistance.

8. The device of claim 1, wherein the sensor array is contained in a housing that includes a cable for connecting the array to the device and an information storage device so that information about the calibration of the sensor array is included in one of the housing or the cable.

9. The device of claim 1, wherein the sensors are arrayed on one surface of a strip of electrically insulating material and a heater is aligned with the array on the other side of the electrically insulating strip, and wherein the temperature of the heater is controlled with a temperature control circuit.

10. The device of claim 9, wherein the heater is comprised of two dissimilar metals forming a thermocouple near the array, the heater being a source of heat and simultaneously a temperature measurement point for the temperature control circuit.

11. The device of claim 9, wherein two sensing conductors are attached to opposite ends of a heat-generating section of the heater to form heat sensing leads of a four-wire resistance measuring circuit.

12. The device of claim 9, wherein one of the sensors is a thermistor that is a control point for the temperature control circuit and a variable in the determination of gas concentrations.

13. The device of claim 9, wherein the control point temperature is calculated from the sensor resistances.

14. A method for converting the resistances of an array of metal oxide sensors into digital signals, wherein the sensors respond to the concentration of gases surrounding the sensor array, comprising
(a) performing an electronic excitation voltage to each sensor and to a reference resistor associated with that sensor;
(b) outputting from an operational amplifier pair associated with each sensor/resistor pair to a comparator pair signals related to the resistance of the sensor and of the resistor; and
(c) receiving on an input pair of a microcontroller having multiple inputs signals as output by a comparator pair, wherein the microcontroller measures as a digital signal the time required for each comparator to change state after a trigger signal.

15. The method of claim 14, wherein the electronic excitation step comprises providing an excitation voltage comprising a short pulse to each sensor, the pulse being applied for less than 10% of the measurement time for each sensor.

16. The method of claim 14, wherein the electronic excitation step comprises providing an excitation voltage comprising a constant direct current voltage.

17. The method of claim 14, wherein the resistance of each sensor is converted to a digital number representing the ratio of the sensor resistance to the resistance of the reference resistor.

18. The method of claim 14, wherein the resistance of each sensor is converted to a digital number representing the log of the ratio of the sensor resistance to the resistance of the reference resistor.

19. The method of claim 14, wherein the resistance of each sensor is converted to a digital number representing the numerical log of the sensor resistance.

20. The method of claim 14, wherein the resistance of each sensor is converted to a digital number representing the reciprocal of the sensor resistance.

21. The method of claim 14, further comprising providing a housing that contains the sensor array and includes a cable for connecting the array to the device and an information storage device so that information about the calibration of the sensor array is included in one of the housing or the cable.

22. The method of claim 14, further comprising:
arraying the sensors on one surface of a strip of electrically insulating material;
aligning a heater with the array on the other side of the electrically insulating strip; and
controlling the temperature of the heater with a temperature control circuit.

23. The method of claim 22, wherein the heater is comprised of two dissimilar metals forming a thermocouple near the array, the heater being a source of heat and simultaneously a temperature measurement point for the temperature control circuit.

24. The method of claim 22, further comprising:
attaching two sensing conductors to opposite ends of a heat-generating section of the heater to form heat sensing leads of a four-wire resistance measuring circuit.

25. The method of claim 22, wherein one of the sensors is a thermistor that is a control point for the temperature control circuit and a variable in the determination of gas concentrations.

26. The method of claim 14, further comprising:
arraying a first plurality of sensors on a surface of an electrically insulating material;
arraying a second plurality of sensors on another surface of the electrically insulating material;
aligning a heater within the electrically insulating material, between the sensor arrays; and
controlling the temperature of the heater with a temperature control circuit.

27. The device of claim 1 further comprising means for calculating gas concentrations from the digital signals.

28. The device of claim 1 wherein an operational amplifier pair outputs signals related to the log of the resistance of the sensor and of the resistor, and/or the trigger signal is related to the charging of a capacitor.

29. The device of claim 1 wherein the electronic excitation source provides an excitation voltage to the sensors that periodically reverses polarity.

30. The method of claim 14 further comprising a step of calculating gas concentrations from the digital signals.

* * * * *